United States Patent [19]

Kisalus

[11] Patent Number: 4,900,426

[45] Date of Patent: Feb. 13, 1990

[54] TRIPHENYLPHOSPHINE OXIDE AS AN ETHYLENE FURNACE ANTIFOULANT

[75] Inventor: John C. Kisalus, Houston, Tex.

[73] Assignee: Nalco Chemical Company, Naperville, Ill.

[21] Appl. No.: 332,649

[22] Filed: Apr. 3, 1989

[51] Int. Cl.$^4$ ............................................. C07C 11/04
[52] U.S. Cl. ................................ 208/48 AA; 585/650; 585/648; 208/48 R
[58] Field of Search .................. 208/48 AA; 585/650, 585/648

[56] References Cited

U.S. PATENT DOCUMENTS

| | | | |
|---|---|---|---|
| 3,531,394 | 9/1970 | Koszman | 208/48 AA |
| 3,647,677 | 3/1972 | Wolff et al. | 208/48 AA |
| 4,105,540 | 8/1978 | Weinland | 208/48 AA |
| 4,542,253 | 9/1985 | Kaplan et al. | 585/650 |
| 4,551,227 | 11/1985 | Porter et al. | 208/48 AA |

FOREIGN PATENT DOCUMENTS 935190 10/1973 Canada ........................... 208/48 AA

OTHER PUBLICATIONS

"Kinetics of Coke Deposition in the Thermal Cracking of Propane", by K. M. Sundaram and G. F. Froment, *Chemical Engineering Science*, 1979, vol. 34, pp. 635–644, Aug.

"Coke Deposition in the Thermal Cracking of Ethane", by K. M. Sundaram, P. S. Van Damme and G. F. Froment, *AIChE Journal*, Nov., 1981, vol. 27, No. 6, pp. 946–951.

*Primary Examiner*—Helane Myers
*Attorney, Agent, or Firm*—John G. Premo; Anthony L. Cupoli; Donald G. Epple

[57] ABSTRACT

Triphenylphosphine oxide prevents fouling in ethylene furnaces.

1 Claim, 4 Drawing Sheets

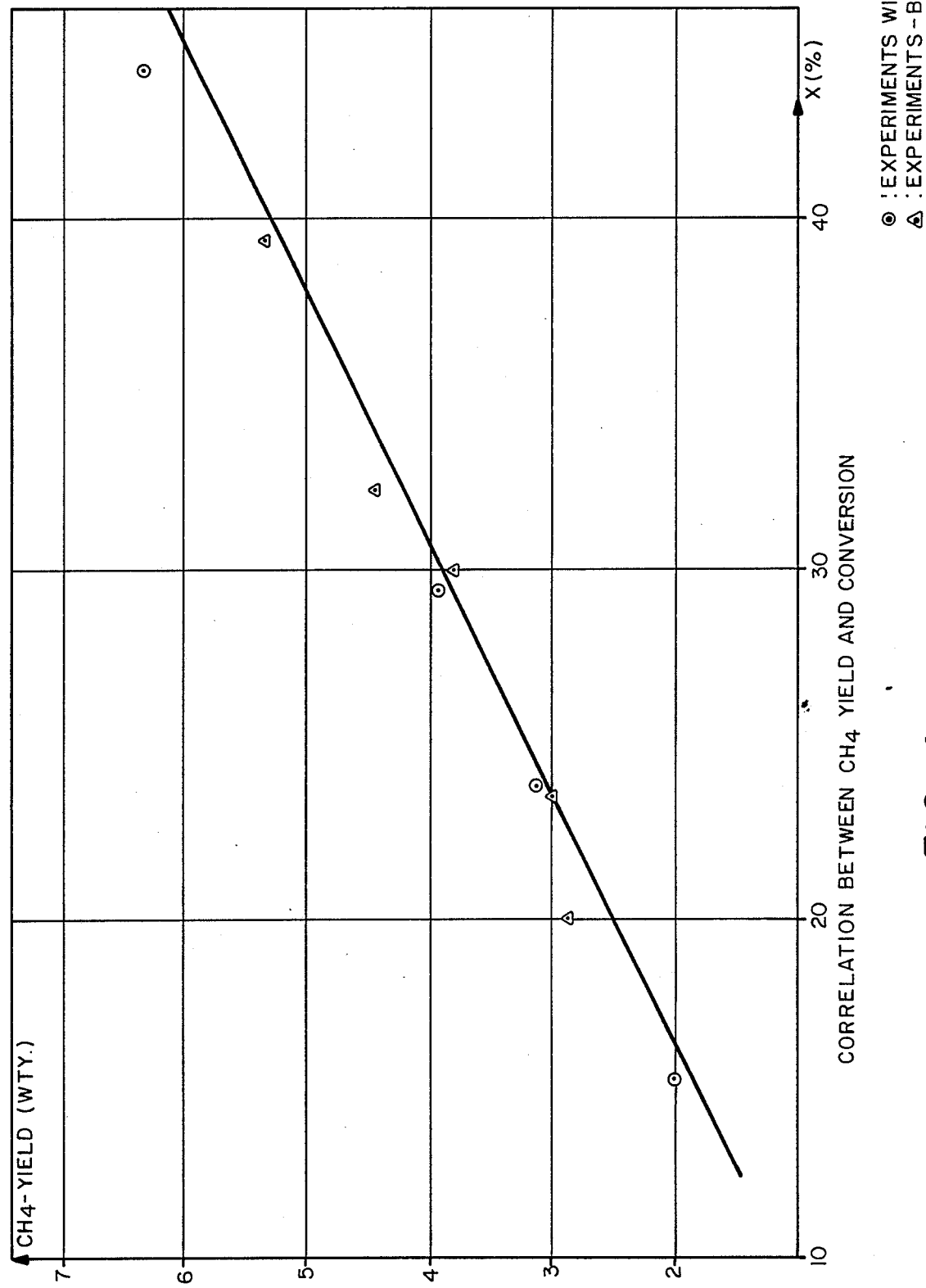

TRIPHENYLPHOSPHINE OXIDE AS AN ETHYLENE FURNACE ANTIFOULANT

INTRODUCTION

Ethylene manufacture entails the use of pyrolysis or "cracking" furnace to manufacture ethylene from various gaseous and liquid petroleum feed stocks. Typical gaseous feed stocks include ethane, propane, butane and mixtures thereof. Typical liquid feed stocks include naphthas, kerosene, gas oil and crude oil.

Fouling of the cracking furnace coils and transfer line exchangers (TLE's) occurs due to coking and polymer deposition. The fouling problem probably is the major operational difficulty experienced in running an ethylene plant. Depending on deposition rate, ethylene furnaces must be periodically shut down for cleaning. In addition to periodic cleaning, "crash shut downs" are sometimes required due to dangerous increases in pressure or temperatures resulting from deposit build-up on furnace coils and TLE's. Cleaning operations are carried out either mechanically or by steam/air decoking.

Run lengths for ethylene furnaces average from one week to three months depending in part upon the rate of fouling of the furnace coils and TLE's. This fouling rate is in turn dependent upon the nature of the feed stock as well as upon furnace design and operating parameters. In general, however, heavier feed stocks and higher cracking severity result in an increased rate of furnace and TLE fouling.

In recent years, amine neutralized sulfonate treatments have been used in some ethylene plants to reduce furnace coil fouling. These compounds, however, have failed to prevent coking and fouling of TLE's immediately down stream of the furnace. The failure in respect of the TLE's may be due to premature degradation of the treatments in the ethylene furnace which sees temperatures in the range 1,000°–1,700° F.

PRIOR ART

U.S. Pat. No. 4,105,540 teaches that phosphate and phosphite mono and diesters in small amounts function as anti-foulant additives in ethylene cracking furnace which are subjected to elevated temperature from about 500°–1,700° F.

U.S. Pat. No. 4,542,253 discloses that certain amine neutralization products of the compounds disclosed in U.S. Pat. No. 4,105,540 provide an improved ethylene cracking furnace anti-foulant.

The abstract of U.S. Pat. No. 4,551,227 describes the invention therein and reads as follows:

"The formation of carbon on metals exposed to hydrocarbons in a thermal cracking process is reduced by contacting such metals with an antifoulant selected from the group consisting of a combination of tin and phosphorus, a combination of phosphorus and antimony and a combination of tin, antimony and phosphorus.

U.S. Pat. No. 3,647,677 indicates that elemental phosphorus prevents coke formation in refining units.

U.S. Pat. No. 3,531,394 shows certain phosphorus compounds as being anti-foulants in steam cracking processes.

The use of triphenylphosphine as an ethylene furnace antifoulant is disclosed in my U.S. application Ser. No. 238,784, filed Aug. 31, 1988 and entitled "Use of Triphenylphosphine as an Ethylene Furnace Antifoulant".

As will be demonstrated hereafter, not all phosphorus-containing compounds provided equal protection to ethylene cracking furnace in the prevention of coke formation therein.

THE DRAWINGS

Figure 3:
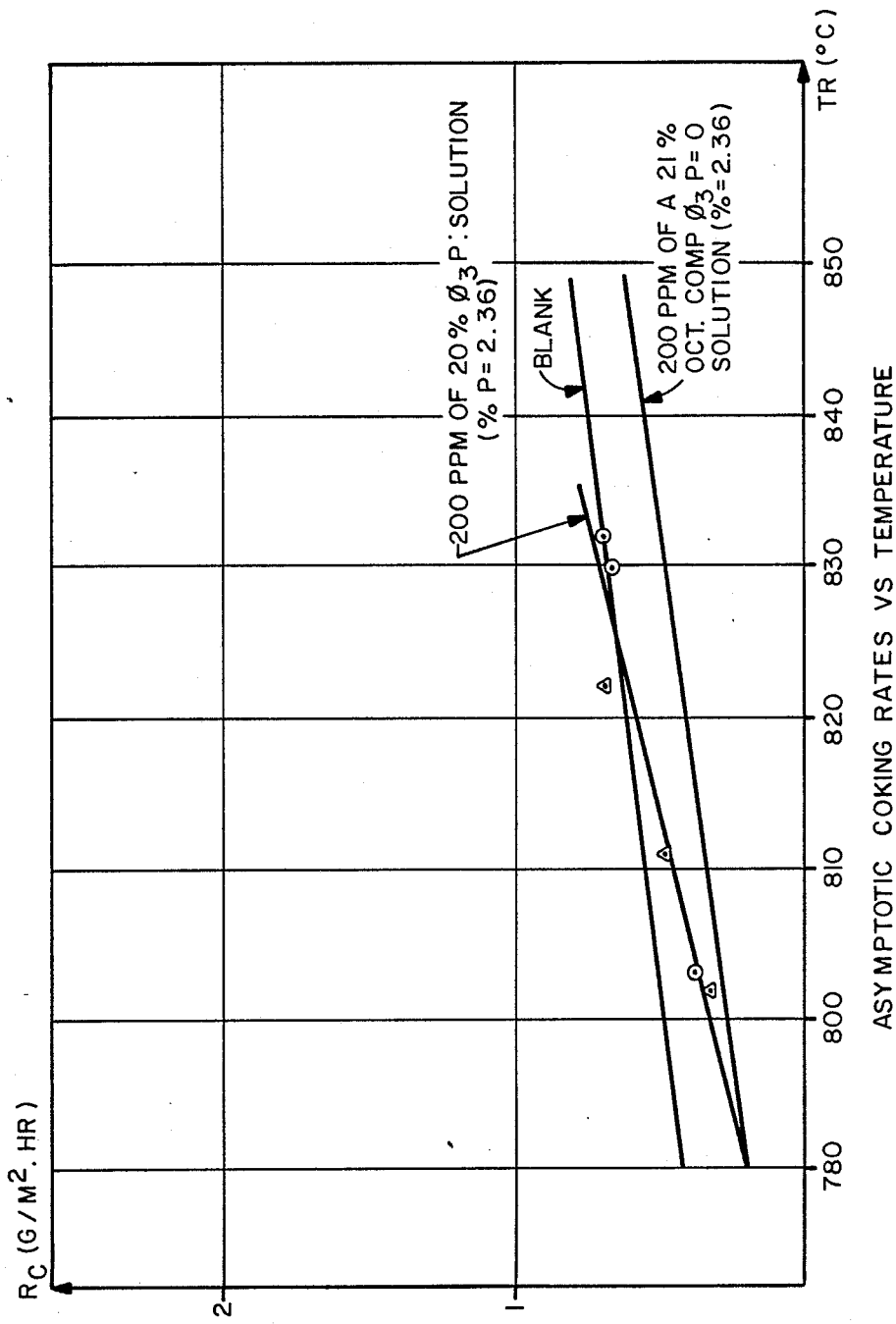

FIG. 3 compares the effect of triphenylphosphine vs. triphenylphosphine oxide on the asymptotic coking rates.

FIG. 4 shows correlation between $CH_4$ yield and conversion.

THE INVENTION

The invention comprises a method for reducing fouling in ethylene cracking furnace using petroleum feed stock which comprises treating the petroleum feed stock with an anti-fouling amount of triphenylphosphine oxide.

THE DOSAGE

The dosage involves treating the feed stock with at least 10 ppm and preferably 25–100 ppm of triphenylphosphine oxide. In addition, it is preferred that plant equipment surfaces be pretreated with this compound.

THE EVALUATION OF THE INVENTION

The test method involved the utilization of a laboratory reactor which duplicated the conditions found in an ethylene cracking furnace. For details see the publications "Kinetics of Coke Deposition in the Thermal Cracking of Propane", K. M. Sundaram and G. F. Froment, *Chemical Engineering Science*, 1979, Vol., 34 pp. 635–644; and "Coke Deposition in the Thermal Cracking of Ethane", K. M. Sundaram, P. S. VanDamme, and G. F. Froment, *AIChE Journal*, November, 1981, Vol. 27, No. 6., pg. 946.

Experimental Conditions continuous addition of 200 ppm triphenylphosphine oxide solution of some 20% active substance a new pretreated, Inconel 600 cylinder

| | |
|---|---|
| Hexane flow | 60 ml/hr |
| Water flow | 20 ml/hr |
| Ve/Fo[1] | 41 L.s/mol |
| dil. water | 0.5 kg/kg |

[1]Ve/Fo is equivalent reactor volume (Ve) to initial molar flow rate of hydrocarbons (Fo) ratio. Reference can be found in Chem. Eng. Sci. 34, 635, (1979), by K. M. Sundaram, and G. F. Froment, and AICHE J., 27, 946 (1981), by K. M. Sundaram, P. S. VanDamme and G. F. Froment.

Blank Experiments

Figure 1:
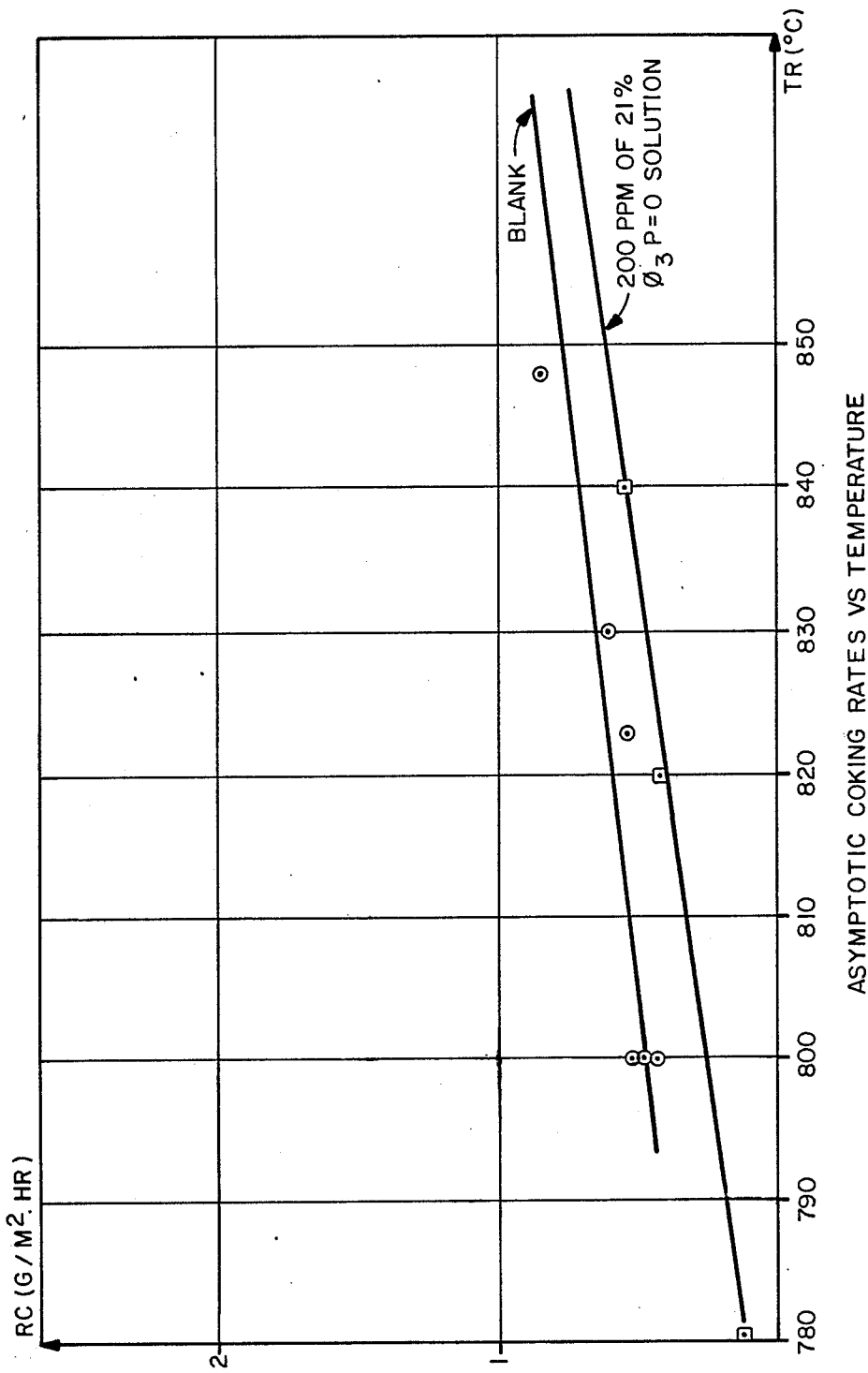
FIG. 1 shows the comparison between the asymptotic coking rates in function of temperature for blank experiments and experiments with continuous addition of triphenylphosphine oxide.

The blank coking rates are shown in FIG. 1.

To check the reproducibility of the results, three experiments were carried out at a reference temperature of 800° C. using the same cylinder. These values are shown in Table I.

As can be seen in FIG. 1, the coking rates of the reactor are low.

The Investigation of the Additive Triphenylphosphine Oxide

A solution of triphenylphosphine oxide, containing 2.36% P was prepared to relate its effectiveness to triphenylphosphine. A 200 ppm of a 21% active substance triphenylphosphine oxide solution in hexane was used (continuous addition—the injected amount of P is the same as in the case of triphenylphosphine).

FIG. 1 shows the effectiveness of the additive by comparing asymptotic coking rates of blank runs with those obtained from continuous addition experiments of triphenylphosphine oxide.

Figure 2:
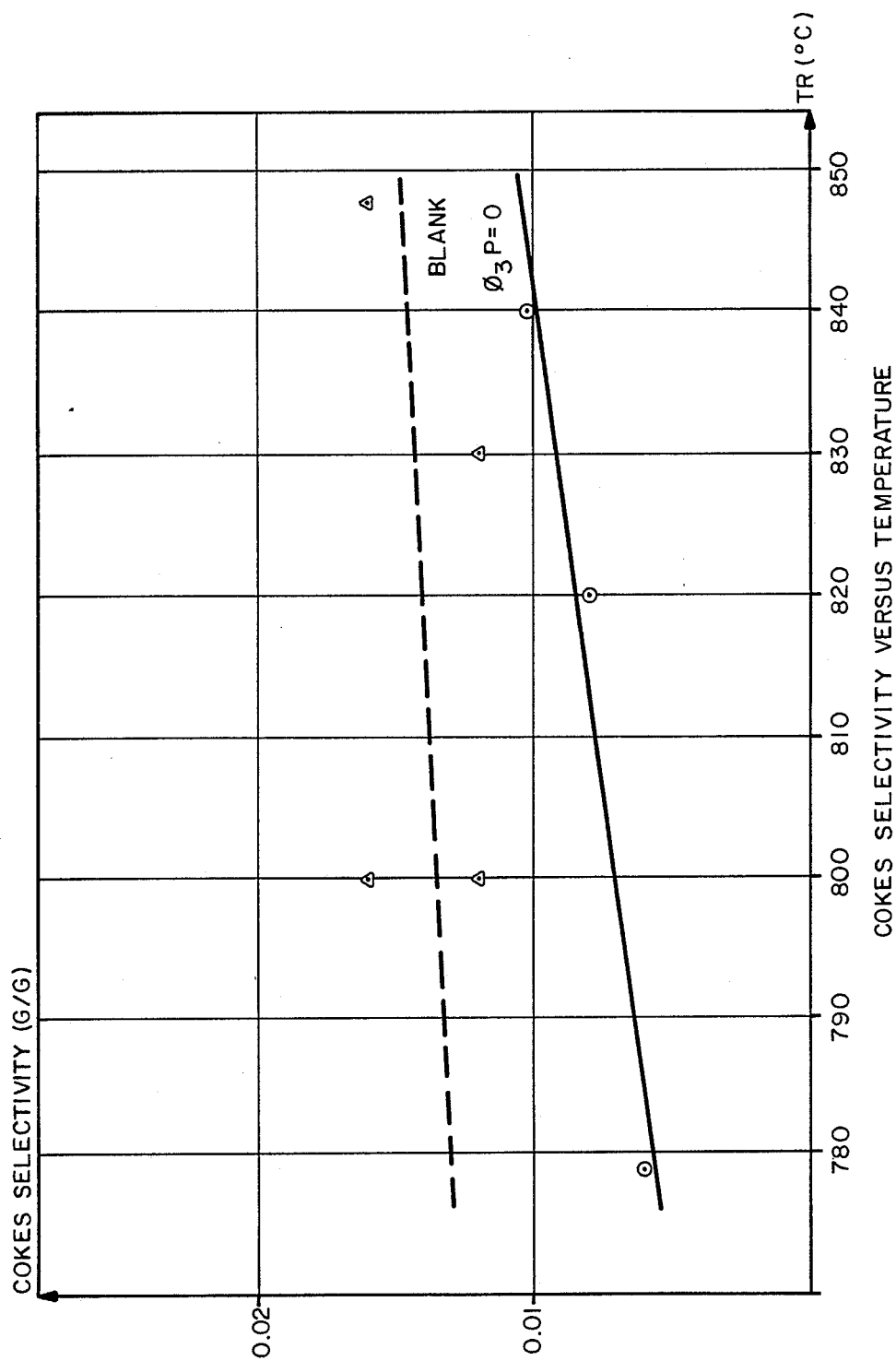
FIG. 2 shows cokes selectivity versus temperature.

Coke selectivity versus Temperature is plotted in FIG. 2.

FIG. 3 compares the effect of triphenylphosphine vs. triphenylphosphine oxide on the asymptotic coking rates.

FIG. 4 shows correlation between $CH_4$ yield and conversion.

TABLE I*

| Temp. (°C.) | Rc g/(m2 · hr) | Conv. (%) | Coke Sel. (g/g) |
|---|---|---|---|
| 830 | 0.60 | 29.8 | 0.012 |
| 848 | 0.83 | 32.1 | 0.016 |
| 800 | 0.47 | — | — |
| 800 | 0.46 | 23.5 | 0.012 |
| 800 | 0.49 | 19.9 | 0.016 |
| 800 | 0.48 | — | — |

TABLE II*

| Temp. (°C.) | Rc g/(m2 · hr) | Coke Sel. (g/g) | Conv. (%) |
|---|---|---|---|
| 779 | 0.116 | 0.005 | 15.2 |
| 840 | 0.469 | 0.010 | 29.2 |
| 820 | 0.403 | — | — |

*Table II: Values of the experiments with the additive triphenylphosphine oxide.

Having thus described my invention, it is claimed as follows:

1. A method for reducing fouling in ethylene cracking furnaces using petroleum feed stock which comprises the petroleum feed stock with an anti-fouling amount of triphenylphosphine oxide.

* * * * *